United States Patent [19]
Droescher et al.

[11] Patent Number: 5,914,325
[45] Date of Patent: Jun. 22, 1999

[54] STEROIDS WITH RADICAL-ATTRACTING AROMATIC SUBSTITUENTS, PROCESS FOR THE PRODUCTION THEREOF AND PHARMACEUTICAL COMPOUNDS CONTAINING THE SAID SUBSTANCES

[75] Inventors: Peter Droescher, Weimar; Bernd Menzenbach; Kurt Ponsold, both of Jona; Bernd Undeutsch; Michael Oettel, both of Jena; Wolfgang Römer, Jona; Günter Kaufmann; Jens Schröder, both of Jena, all of Germany

[73] Assignee: Jenapharm GmbH, Jena, Germany

[21] Appl. No.: 08/646,252

[22] PCT Filed: Nov. 8, 1994

[86] PCT No.: PCT/DE94/01310

§ 371 Date: Jul. 8, 1996

§ 102(e) Date: Jul. 8, 1996

[87] PCT Pub. No.: WO95/13287

PCT Pub. Date: May 18, 1995

[30] Foreign Application Priority Data

Nov. 10, 1993 [DE] Germany ............... 43 38 316

[51] Int. Cl.⁶ ............... A61K 31/56; C07J 3/00
[52] U.S. Cl. ............... 514/182; 552/610; 552/626; 552/630
[58] Field of Search ............... 552/505, 522, 552/525, 548, 552, 553, 555, 556, 558, 610, 611, 626, 630; 514/182

[56] References Cited

U.S. PATENT DOCUMENTS

| | | | |
|---|---|---|---|
| 3,193,564 | 7/1965 | Counsell et al. | 260/397.5 |
| 5,371,078 | 12/1994 | Clark et al. | 514/182 |

FOREIGN PATENT DOCUMENTS

| | | |
|---|---|---|
| 0389370 | 3/1990 | European Pat. Off. . |
| 0389368 | 9/1990 | European Pat. Off. . |
| 0389369 | 3/1995 | European Pat. Off. . |
| 2640977 | 12/1988 | France . |
| WO 87/01706 | 3/1987 | WIPO . |
| WO 91/11453 | 8/1991 | WIPO . |

OTHER PUBLICATIONS

Inhibition of Peroxidations of Lipids and Membranes by Estrogens. Komur, E. Takahashi, Morita, Tsuchiya, Arakawa, Yamamoto & Niki (1990).

Eicosanoids, Lipid Peroxidation and Cancer. Nigam, McBrien & slater 1988.

Peters et al., "17–desoxy estrogen analogues", J. Med. Chem., vol. 32, pp. 1642–1652, 1989.

*Primary Examiner*—Jose' G. Dees
*Assistant Examiner*—Barbara Badio
*Attorney, Agent, or Firm*—Michael J. Striker

[57] ABSTRACT

Disclosed are estrane derivatives having a radical-attracting aromatic substituent of the general formula $-(CH_2)_n X$ attached to the 17-position of the steroid nucleus, wherein X and n are as defined by the specification. The compounds are useful as antitumor agents and in the treatment of cardiac and circulatory disorders.

4 Claims, No Drawings

STEROIDS WITH RADICAL-ATTRACTING AROMATIC SUBSTITUENTS, PROCESS FOR THE PRODUCTION THEREOF AND PHARMACEUTICAL COMPOUNDS CONTAINING THE SAID SUBSTANCES

This application is a 371 of PCT/DE94/01310 filed Nov. 8, 1994.

BACKGROUND OF THE INVENTION

The invention relates to novel steroids with radical-attracting aromatic substituents, processes for their production, and medications containing these compounds for the prophylaxis and therapy of radical-mediated cell damage.

From professional and patent literature it is known that reactive oxygen species (ROSs), free oxygen radicals and other radial forms play an important role in the occurrence of many kinds of cell damage, such as ischemic and traumatic organ injuries, and inflammatory and toxic processes.

A negative effect of ROSs, free oxygen radicals and other forms of radicals can also be found in brain and spinal column injuries, shock states, stroke, muscular dystrophy, emphysemas, adult respiratory distress syndrome (ARDS), asthma, aging processes, in tissue damage after myocardial infarction, damage from toxic processes and radiation, burns, and transplant-dictated immune reactions. Among other factors, lipid peroxidation and the oxidation of low-density lipoprotein (LDL) cholesterol, combined with irreversible membrane and endothelial damage are the starting point for such radical-mediated cell damage.

It is also known that lipophilic substances, such as lipophilic steroids, with radical-scavenging ("radical-trapping") properties can be suitable for prophylaxis and therapy of radical-mediated cell damage.

Unlike the known low-molecular phenolic antioxidants, these lipophilic steroids are transported with a certain selectivity into the region of the cell membrane or endothelium, where they can develop their efficacy.

The therapeutic utility is determined by the action spectrum of the respective substance.

International Patents WO 87/01716 and WO 91/11453, European Patents EP 0 389 368, EP 0 389 369, and EP 0 389 370, and French Patent FR 2 640 977, for instance, describe steroids with scavenger properties.

WO 87/01716, WO 91/11453 and EP 0 389 368/. . . 369/. . . 370 describe steroids which a the terminal carbon atom of the $C_{17}$ side chain contain an amino group, which can be substituted or can be a component of a heterocyclic ring system.

In FR 2 640 977, a structural type is shown that has a substituted phenyl ring in the β position on the $C_{11}$ atom.

It is shown in J. Phys. Org. Chem. 3 (1990), 309–315 that estrogens, and especially catechol estrogens, can act as radical catchers. Estradiol, estrone, estriol and 2-hydroxyestradiol inhibit peroxidation in vitro and in vivo.

SUMMARY OF THE INVENTION

The object of the invention is to provide novel steroids with radical-attracting aromatic substituents and processes for their production.

A further object of the invention is to disclose medications that contain these compounds.

According to the invention, this object is attained in the novel steroids with radical-attracting aromatic substituents of general formula I and general formula II of the claims appended hereinbelow have been discovered.

The radical-attracting aromatic substituent Y can be represented as a component of a substituent of the following general formula:

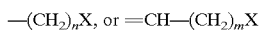

where X=Y, OY, SY, SeY, NHY,
and n=0–5; m=n–1

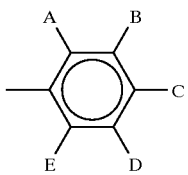

where A-E independently of one another represent H, alkyl, Oalkyl, Oacyl, OH or one of the substituents B, C, D=$NR_2$, where R=alkyl, and each of the other four substituents are hydrogen.

The most highly preferred compounds of the steroids of the invention with radical-attracting aromatic substituents are 17α-4'-Hydroxyphenylmercaptomethyl-17-hydroxyestr-4-ene-3-one,
17α-4'-Hydroxyphenylmercaptomethyl-3,3-dimethoxyestr-5(10)-ene-17-ol,
17α-4'-N,N-Dimethylaminophenylmethyl-17-hydroxyestr-4-ene-3-one,
17α-4'-N,N-Dimethylphenylmethyl-3,3-dimethoxyestr-5(10)-ene-17-ol,
17α-4'-Hydroxyphenylmethyl-17-hydroxyestr-4-ene-3-one,
17α-2',6'-Dimethyl-4'-hydroxyphenylmethyl-17-hydroxyestr-4-ene-3-one,
17α-4'-Hydroxyphenoxymethyl-17-hydroxyestr-4-ene-3-one,
17α-4'-Hydroxyphenylmercaptomethyl-17-hydroxy-5α-androstan-3-one,
17α-4'-Hydroxyphenylmercaptomethyl-17-hydroxyandrost-4-ene-3-one,
17α-4'-Hydroxyphenylmercaptomethyl-17-hydroxy-1α-methyl-5α-androstan-3-one,
6β-4'-Hydroxyphenyl-17β-hydroxyandrost-4-ene-3-one,
6β-4'-Hydroxyphenyl-5α,17β-dihydroxyandrostan-3-one,
6-2',6'-Dimethyl-4'-hydroxyphenylestra-1,3,5(10),6-tetraene-3,17β-diol,
17-4'-N,N-Dimethylaminophenylestra-1,3,5(10),16-tetraene-3-ol,
17α-4'-N,N-Dimethylaminophenylestra-1,3,5(10)-triene-3,17-diol,
6-4'-N,N-Dimethylaminophenylestra-1,3,5(10),6-tetraene-3,17β-diol,
17α-4'-N,N-Dimethylaminophenylmethylestra-1,3,5(10)-triene-3,17-diol,
17α-4'-N,N-Dimethylaminophenylmethylestra-1,3,5(10),9(11)-tetraene-3,17-diol,
17α-4'-N,N-Dimethylaminophenylmethyl-3-methoxyestra-1,3,5(10)-triene-17-ol,
17α-4'-Hydroxyphenylmethylestra-1,3,5(10)-triene-3,17-diol, 17α-4'-Hydroxyphenylmethylestra-1,3,5(10),9(11)-tetraene-3,17-diol,
17α-4'-Hydroxyphenylmercaptomethylestra-1,3,5(10)-triene-3,17-diol,
17α-4'-Hydroxyphenylmercaptomethylestra-1,3,5(10),9(11)-tetraene-3,17-diol,
17α-4'-Hydroxyphenylmercaptomethyl-3-methoxyestra-1,3,5(10)-triene-17-ol,
17α-4'-Hydroxyphenylmethyl-3-methoxyestra-1,3,5(10)-triene-17-ol,
17α-2',6'-Dimethyl-4'-hydroxyphenylselenomethyl-3-methoxyestra-1,3,5(10)-triene-17-ol,
17α-4'-N,N-Dimethylaminophenylselenomethyl-3-methoxyestra-1,3,5(10)-triene-17-ol,
17α-2',6'-Dimethyl-4'-hydroxyphenylmethyl-3-methoxyestra-1,3,5(10)-triene-17-ol,
17α-2',6'-di-tert.-butyl-4'-hydroxyphenylmethyl-3-methoxy-estra-1,3,5(10)-triene-17-ol,
17α-2',6'-di-tert.-butyl-4'-hydroxyphenylselenomethyl-3-methoxyestra-1,3,5(10)-triene-17-ol and
6α-4'-Hydroxyphenylmercaptomethyl-17-hydroxyandrost-4-ene-3-one.

The invention further relates to a process for producing the steroids of general formulas I and II, which is characterized in that the insertion of the radical-attracting substituents into position 17 of the steroid skeleton is effected via the nucleophilic opening of a 17-spirooxirane or directly by alkylation of the 17-oxo group, and that the direct alkylation of the 17-oxo group is done via the conversion of corresponding metal organyls with cerium(III) salts. The methods of synthesis used in the production of the steroids of the invention are based as a rule on well known steroids with an estrane, androstane, pregnane or cholestane basic skeleton, in which possibly troublesome functional groups, such as hydroxy and oxo groups, are meanwhile protected by known methods, for instance in the form of esters, ethers, silyl ethers, enol ethers or acetals.

The insertion of the radical-attracting substituents into position 17 of the steroid skeleton is effected via the nucleophilic opening of a 17-spirooxirane or directly by alkylation of the 17-oxo group.

Because of the steric hindrance at C17, the insertion of the aromatic substituents Y, where n=0, does not succeed until conversion of the 17-ketone with the corresponding Grignard compound, in the presence of $Ce^{3+}$ below room temperature, in a dipolar-aprotic solvent, preferably THF or diethylene glycol dimethyl ethers.

This kind of procedure is novel for steroids.

However, it is known from the literature that Grignard compounds in the presence of equimolar quantities of Ce(3) salts are quite suitable for alkylating readily enolizable or sterically hindered ketones.

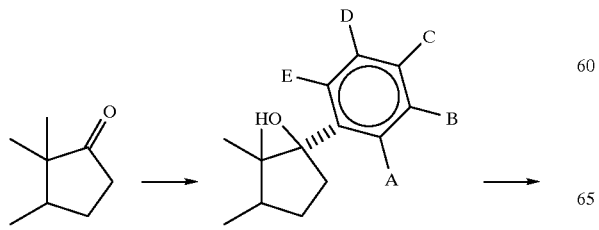

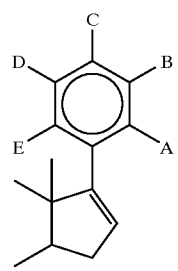

By splitting off of the tertiary benzylic hydroxy group in an acid medium, the corresponding 16,17-unsaturated compounds are obtained. 17-spirooxiranes are converted into corresponding 17α-substituted 17-ols with nucleophilic agents under neutral or alkaline conditions in organic solvents at room temperature.

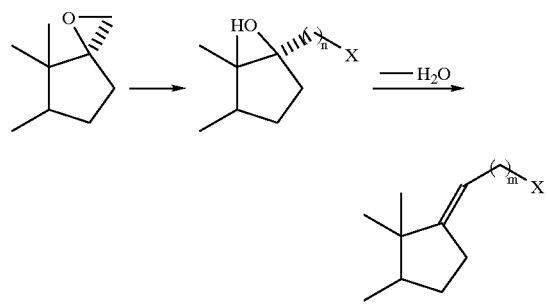

By well known methods for splitting off tertiary hydroxy groups, such as heating in an adequately acidic medium, treatment of the corresponding mesylate with a base, or thermal dehydration in DMSO, corresponding olefins can also be obtained.

For synthesizing the 17-spirooxiranes, the 17-ketones, such as the steroids listed below, are reacted with dimethyl sulfonium methylide in dipolar-aprotic solvents or mixtures thereof, in analogy with the method described by Ponsold et al in Z. Chem. 11; 1972; p. 106.

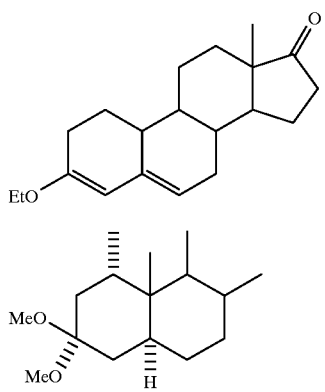

-continued

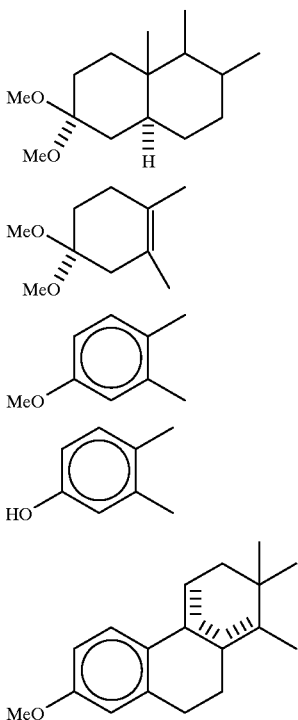

As nucleophilic agents for splitting the 17-spirooxiranes of the structures shown above, substituted phenylates and thiophenylates and suitable metallo-organic reagents, such as Grignard compounds and their O—, S— and Se-analogs can be considered.

The choice of solvent in the reaction of the spirooxiranes with the phenylates and thiophenylates depends not only on its suitability for the SN2 reactions but also on the solubilities of the applicable oxiranes and of the nucleophilic agent used and can vary within wide limits.

Aprotic solvents, such as ether, DMSO or DMF, are highly suitable.

In reactions with metallo-organic reagents, ethers and preferably cyclic ethers are the most suitable.

3-ethoxy and 3,3-dimethoxy compounds are also hydrolyzed to make the corresponding keto compounds.

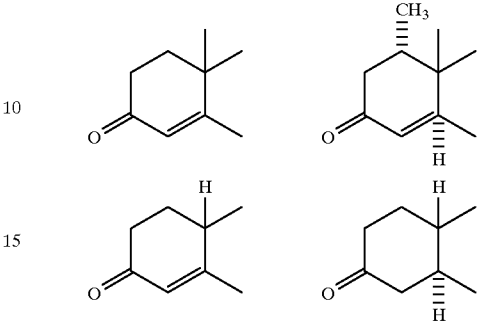

The splitting generally occurs in such a way that the compounds are dissolved or suspended in a water-miscible solvent, such as acetone, methanol or ethanol, and an aqueous solution is added to an acid.

As the acids, above all such organic acids as p-toluene sulfonic acid, acetic acid or oxalic acid are used, but dilute mineral acids such as hydrochloric acid, hydrobromic acid, sulfuric acid or perchloric acid are also suitable.

Silyl ether functions, which serve the purpose of temporary masking of the phenolic hydroxy groups in reactions with metallo-organic reagents, are cancelled out again by the usual methods found in the literature.

To insert the radical-attracting substituents into position 6 of steroids with an aromatic A-ring, the corresponding 6-oxo steroid is preferably reacted with the Grignard compound in the presence of $Ce^{3+}$ at temperatures below room temperature in dipolar-aprotic solvents, preferably THF or diethylene glycol dimethyl ethers.

By using the intermediate cerium compounds produced, which have lower alkalinity than the Grignard compounds, enolization of the 6-ketone is effectively repressed.

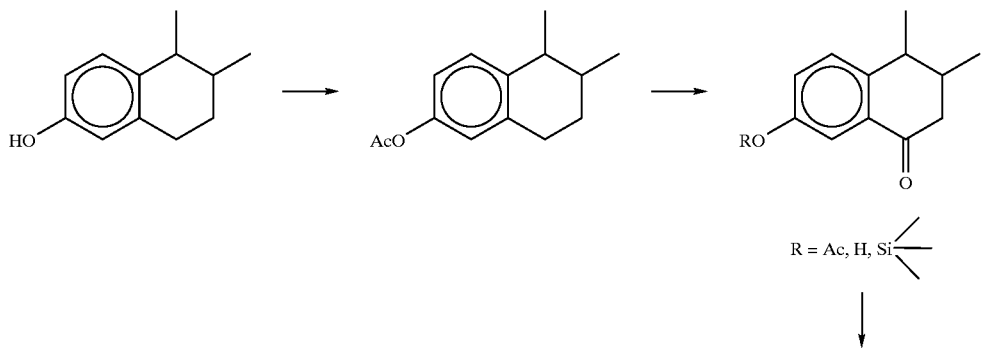

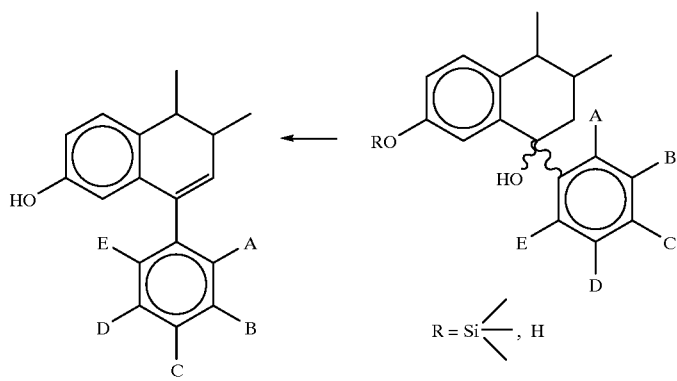

By treatment with acids in organic solvents at room temperature, for instance, water can be split off and the 6-dehydro compound can be obtained.

The 6-oxo steroid serving as starting material can be produced by various known methods of oxidation, such as with chromium (VI) oxide/dimethylpyrazol in methylene chloride.

In steroids without an aromatic A-ring, the radical-attracting aromatic substituent is inserted by nucleophilic spitting, for instance by way of the 5,6α-epoxide or the 6,7α-epoxide, which is readily accessible from the corresponding 3-oxo-4,6-dienes with sodium hydroxide and hydrogen peroxide.

The sequences leading by way of the 5,6α-epoxide, particularly for the preparation of 6α-methyl steroids of the androstane and pregnane series, are known.

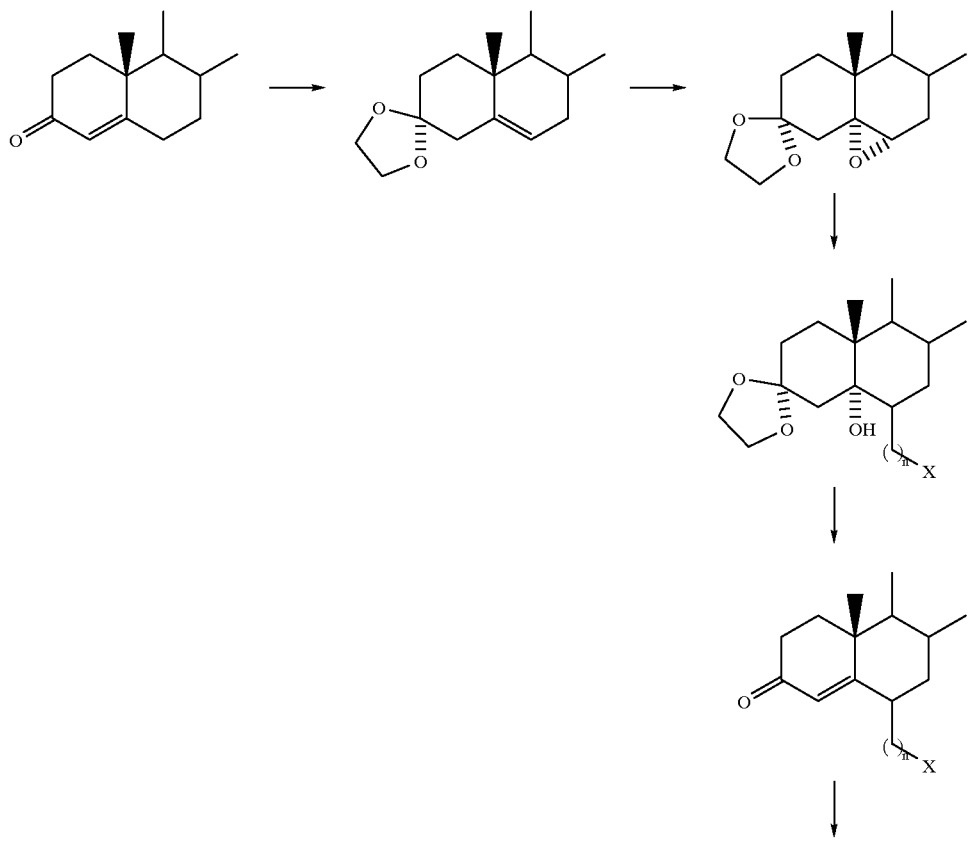

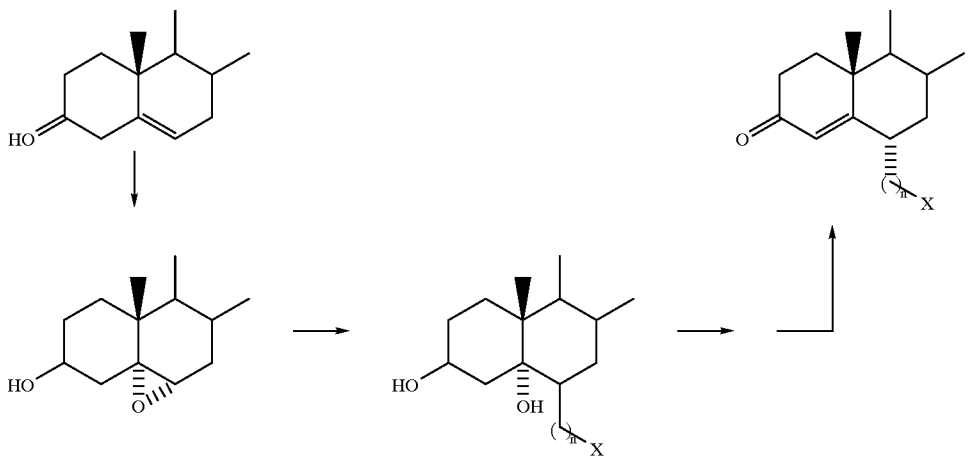

Positions 1 and 7 of the steroid skeleton may be linked to radical-attracting aromatic substituents by 1,4- or 1,6-addition of the nucleophils to the α,β- or α,β,gamma,δ-unsaturated 3-oxo steroids.

The conversion is effected with C-nucleophils [$(CH2)_n X$, where $n \neq 0$] under strictly aprotic conditions with suitable Grignard compounds with copper(I) catalysis, or directly with the organocuprates in solvents such as THF, diethylene glycol dimethyl ethers, toluene, preferably at low temperatures, in a manner known per se.

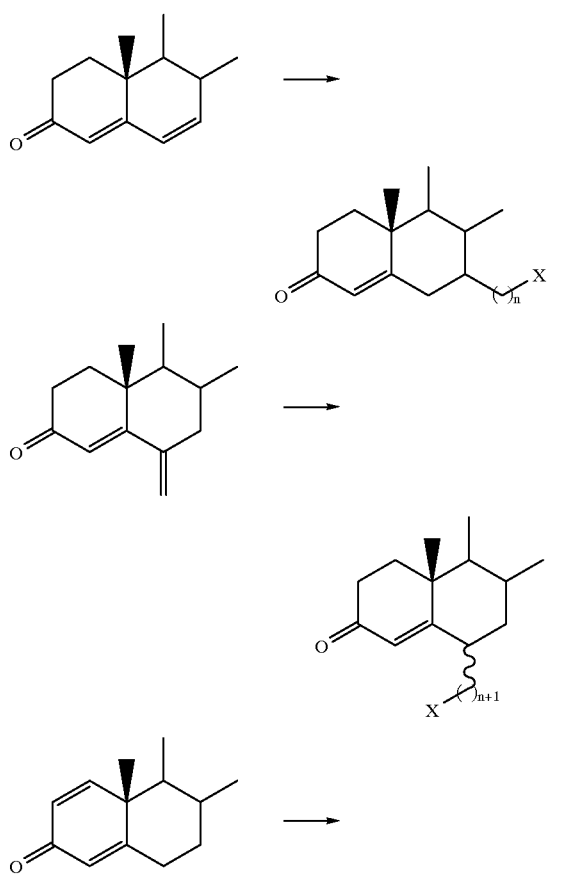

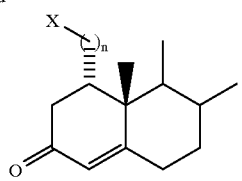

The exclusion of protic solvents is unnecessary in the case of other nucleophils (n=0 and X=OY, SY, SeY, NHY); both protic (alcohols) and nonpolar (toluene) or dipolar-aprotic (DMSO, THF) solvents may be used. The reaction temperature is not, as in the case of the C-nucleophils, limited by the instability of the copper organyls.

The reactions are catalyzed with suitable bases, such as triton B, copper(II) acetate, and amines.

The substitution at the C15 can be attained by the same principle (U.S. Pat. Nos. 3,173,932 and 3,766,224).

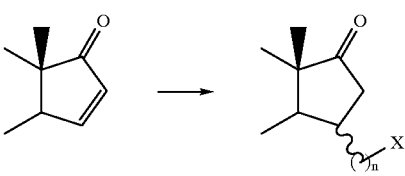

The preparation of the 15-en-17-one is known from the literature and is effected for instance by α-bromination of the 17-ketone, or its ethylene ketal, and ensuing dehydrobromination.

Various alternatives exist for the use of nucleophilic epoxide openings reactions for inserting radical-active aromatic substituents into position 16. 15,16β-epoxy-17β-hydroxy steroids, which can be produced by known methods from the aforementioned 15-dehydro-17-oxosteroid after 1,2-reduction of the oxo group with complex hydrides by oxidation with an organic per-acid; 16,17β-epoxy steroids, which are isolated from the corresponding 16-dehydro steroids by halogen hydrin addition and ensuing dehydrohalogenation in the presence of bases, and the epimeric 16,17α-epoxy steroids, which can be obtained from the 16-dehydro steroid with organic peracids, can be used.

In contrast to the other two types of epoxide, the 16,17β-epoxy steroid furnishes mixtures of 16α- and 17α- substituted products, so that the other two epoxides (16,17α- and 17β-hydroxy-15,16β-epoxy steroids) are used as preferred starting substances.

The reaction with the nucleophilic agents takes place under conditions of the kind already described with respect to the opening of the 5,6α-epoxides.

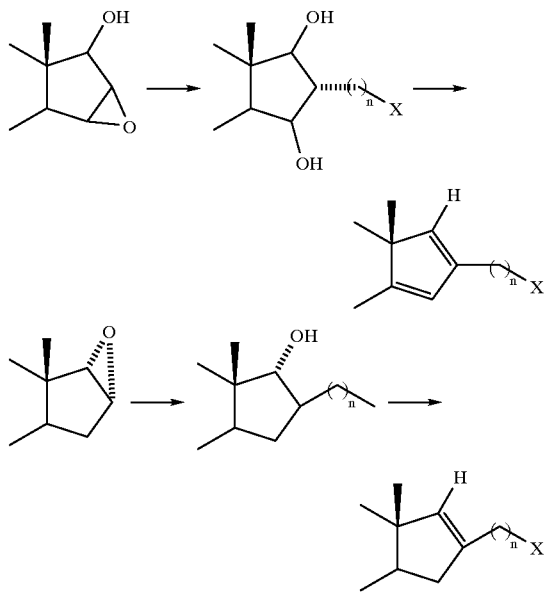

Splitting off of the secondary 17-hydroxy group using typical conditions leads to the various D-ring olefins.

Starting with 19 nor-steroids with 5(10)-double bonding, a radical-attracting aromatic substituent can also be inserted into position 10. The 5,10α-epoxy steroid, which is accessible with a good yield via halogen hydrin addition and basic cyclizing, can be opened nucleophilically.

Oxidation under acid conditions directly produces the 3-oxo-4-dehydro steroid substituted in the 10 position (Ponsold et al; Tetrh. Lett. 1970; page 1125).

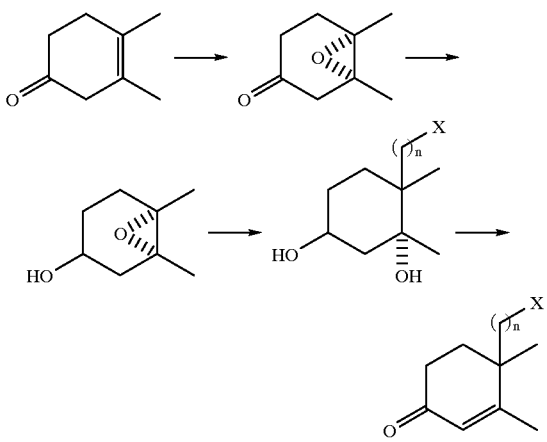

According to the invention, the radical-attracting substituents can also be coupled to the C22 of the 20-methylpregnane system. Readily accessible starting materials that can be used include 20-hydroxymethyl-1,4-pregnadiene-3-one or 3-hydroxy-20-hydroxymethyl-1,3,5(10)-pregnatriene.

For instance, after protection of the 3-hydroxy group by nucleophilic substitution of 22-tosylate or 22-halide, made by known methods, with an alcoholate, thiolate, or a carbanionoid reagent, such as a Grignard compound, with copper(I) catalysis, the radical-attracting substituent can be inserted.

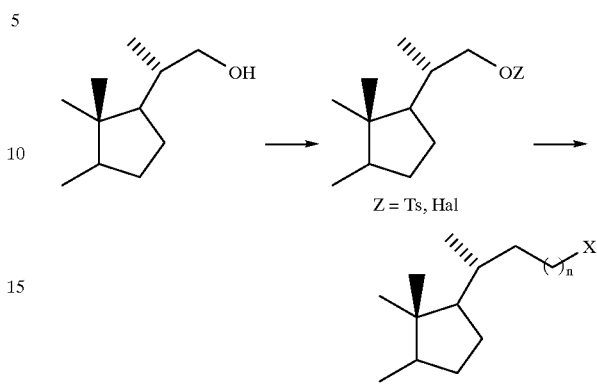

Selenoaryls can be prepared as follows, in accordance with D. G. Forster et al, Org. Synth. Coll., Vol. IV, 1964, p. 771:

Aryl magnesium halides are converted, with elemental selenium via the polyselenides thus produced, into aryl selenomagnesium halides, which are then hydrolyzed.

According to the invention, the seleno steroids described in claims 1 and 2, among others, are not obtained by reacting seleno aryls with electrophilic steroid combinations; instead, aryl selenomagnesium halides are reacted in situ with the corresponding steroidal electrophils, such as an oxirane or sulfonic acid ester.

These reactions of aryl selenomagnesium halides with steroids enable wide variation of seleno substituents at the various positions of the steroid molecule.

From the literature (I. M. Akhmedov et al, Zh. Org. Khim, 14 (4), 1978, p. 881, only reactions of aryl selenomagnesium bromides with epichlorohydrin are known.

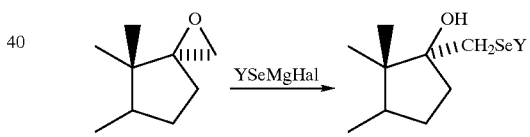

The subject of the present invention also includes pharmaceutical preparations for oral and parenteral, including topical, rectal, subcutaneous, intravenous, intramuscular, intraperitoneal, intranasal, intravaginal, intrabuccal or sublingual application, which in addition to typical vehicles and diluents contain a compound recited in claim 1 or 2 as an active ingredient.

The medications of the invention are prepared in a known manner with the usual solid or liquid vehicles or diluents and with the typically used pharmaceutical-technical adjuvants, depending on the desired type of application and with suitable dosing.

The advantages of the invention arise substantially from the fact that novel steroids with radical-attracting aromatic substituents have been discovered,
  whose action profile differs from that of the known antioxidants, including vitamin E;
  which can be used as active ingredients in pharmaceutical preparations for prophylaxis and therapy of radical-mediated cell damage; and
  which in comparison with conventional preparations exhibit high efficacy.

The advantageous action of the systems according to the invention as inhibitors of lipid peroxidation and LDL oxidation are demonstrated in Table 1 and Table 2.

As comparisons to the systems of the invention, 17β-estradiol, estriol, U-78517F and vitamin E are likewise shown in Table 1 and Table 2.

The measurement of the in vitro inhibition of lipid peroxidation was done by means of the thiobarbituric acid test.

The lipid peroxidation-inhibiting action of the respective compound is characterized with the statement of the $IC_{50}$ inhibition values. $IC_{50}$ indicates the quantity of substance to be added in order to attain a 50% inhibition of lipid peroxidation (Table 1).

The measurement of in vitro inhibition of LDL oxidation was performed in accordance with Esterbauer et al (1988): Effect of peroxidative conditions on human plasma low density lipoproteins. In: Eicosanoids, lipid peroxidation and cancer (ed. Nigam et al), pages 203–214, Springer-Verlag, Berlin, Heidelberg, New York.

The values listed in Table 2 for inhibition of LDL oxidation represent examples for cardiovascular activities.

TABLE 1

Lipid peroxidation inhibition of selected compounds

| Compound | Lipid peroxidation inhibition [$IC_{50}$: μM] |
|---|---|
| 17β-Estradiol | 12.4 |
| Estriol | 22.5 |
| Vitamin E | 132.0 |
| 17α-4'-Hydroxyphenylmercaptomethyl-17-hydroxyestr-4-ene-3-one | 8.6 |
| 17α-4'-Hydroxyphenylmercaptomethyl-3,3-dimethoxyestr-5(10)-ene-17-ol | 1.46 |
| 17α-4'-N,N-Dimethylaminophenylmethyl-17-hydroxyestr-4-ene-3-one | >10 |
| 17α-4'-N,N-Dimethylphenylmethyl-3,3-dimethoxyestr-5(10)-ene-17-ol | 5.5 |
| 17α-4'-Hydroxyphenylmethyl-17-hydroxyestr-4-ene-3-one | 50 |
| 17α-2',6'-Dimethyl-4'-hydroxyphenylmethyl-17-hydroxyestr-4-ene-3-one | 1.92 |
| 17α-4'-Hydroxyphenoxymethyl-17-hydroxyestr-4-ene-3-one | 10.1 |
| 17α-4'-Hydroxyphenylmercaptomethyl-17-hydroxy-5α-androstan-3-one | 4.75 |
| 17α-4'-Hydroxyphenylmercaptomethyl-17-hydroxyandrost-4-ene-3-one | 10.94 |
| 17α-4'-Hydroxyphenylmercaptomethyl-17-hydroxy-1α-methyl-5α-androstan-3-one | 3.82 |
| 6β-4'-Hydroxyphenyl-17β-hydroxyandrost-4-ene-3-one | 60 |
| 6β-4'-Hydroxyphenyl-5α,17β-dihydroxyandrostan-3-one | |
| 6-2',6'-Dimethyl-4'-hydroxyphenylestra-1,3,5(10),6-tetraene-3,17β-diol | 0.95 |
| 17-4'-N,N-Dimethylaminophenylestra-1,3,5(10),16-tetraene-3-ol | 4.5 |
| 17α-4'-N,N-Dimethylaminophenylestra-1,3,5(10)-triene-3,17-diol | 0.95 |
| 6-4'-N,N-Dimethylaminophenylestra-1,3,5(10),6-tetraene-3,17β-diol | 2.75 |
| 17α-4'-N,N-Dimethylaminophenylmethylestra-1,3,5(10)-triene-3,17-diol | 3.53 |
| 17α-4'-N,N-Dimethylaminophenylmethylestra-1,3,5(10),9(11)-tetraene-3,17-diol | 2.1 |
| 17α-4'-N,N-Dimethylaminophenylmethyl-3-methoxyestra-1,3,5(10)-triene-17-ol | 1.64 |
| 17α-4'-Hydroxyphenylmethylestra-1,3,5(10)-triene-3,17-diol | 4.03 |
| 17α-4'-Hydroxyphenylmethylestra-1,3,5(10),9(11)-tetraene-3,17-diol | 0.32 |
| 17α-4'-Hydroxyphenylmercaptomethylestra-1,3,5(10)-triene-3,17-diol | 2.2 |
| 17α-4'-Hydroxyphenylmercaptomethylestra-1,3,5(10)9(11)-tetraene-3,17-diol | 0.44 |
| 17α-4'-Hydroxyphenylmercaptomethyl-3-methoxyestra-1,3,5(10)-triene-17-ol | 4.32 |
| 17α-4'-Hydroxyphenylmethyl-3-methoxyestra-1,3,5(10)-triene-17-ol | 2.64 |
| 17α-2',6'-Dimethyl-4'-hydroxyphenylselenomethyl-3-methoxyestra-1,3,5(10)-triene-17-ol | 1.97 |
| 17α-4'-N,N-Dimethylaminophenylselenomethyl-3-methoxyestra-1,3,5(10)-triene-17-ol | 1.33 |
| 17α-2',6'-Dimethyl-4'-hydroxyphenylmethyl-3-methoxyestra-1,3,5(10)-triene-17-ol | 2.34 |
| 17α-2',6'-Di-tert.-butyl-4'-hydroxyphenylmethyl-3-methoxyestra-1,3,5(10)-triene-17-ol | 12.62 |
| 17α2',6'-Di-tert.-butyl-4'-hydroxyphenylselenomethyl-3-methoxyestra-1,3,5(10)-triene-17-ol | 4.97 |

TABLE 2

LDL oxidation inhibition of selected compounds (1 μM)

| Compound | LDL oxidation inhibition (prolongation of lag phase in min) |
|---|---|
| 17β-Estradiol | 40 |
| Estriol | 20 |
| U-78517F | 20 |
| 17α-4'-Hydroxyphenylmercaptomethylestra-1,3,5(10),9(11)-tetraene-3,17-diol | 270 |
| 17α-4'-Hydroxyphenylmethylestra-1,3,5(10),9(11)-tetraene-3,17-diol | 230 |
| 17α-4'-N,N-Dimethylaminophenylmethyl-3-methoxyestra-1,3,5(10)-triene-17-ol | 195 |
| 6-2',6'-Dimethyl-4'-hydroxyphenylestra-1,3,5(10),6-tetraene-3,17β-diol | 180 |
| 17α-4'-N,N-Dimethylaminophenylestra-1,3,5(10)-triene-3,17-diol | 170 |
| 17α-4'-Hydroxyphenylmercaptomethylestra-1,3,5(10)-triene-3,17-diol | 120 |
| 17α-4'-Hydroxyphenylmethylestra-1,3,5(10)-triene-3,17-diol | 125 |

It should be stated that the compounds produced according to the invention have a demonstrably high lipid peroxidation or LDL oxidation inhibition in vitro and hence have the attendant property of being able to act as radical scavengers. They work as well as or better than the respective conventional compounds, 17β-estradiol, estriol, U-78517F, and vitamin E. To achieve the same inhibition action or better inhibition action, less substance is required.

The preparations according to the invention represent both inhibitors of lipid peroxidation and inhibitors of LDL oxidation and are therefore suitable for prophylaxis and therapy of radical-mediated cell damage, such as in the case of spinal trauma, ischemic (thromboembolytic) stroke, ischemia, organ damage in the re-perfusion phase after transplants, chronic-degenerative CNS diseases, senile dementia of the Alzheimer's type (SDAT), asthma, muscular dystrophy, and degenerative neurological diseases, including those in the form of toxic or degenerative CNS states.

The preparations according to the invention likewise prove to be advantageous for prophylaxis and therapy of such diseases, caused by radical-mediated cell damage, as multiple sclerosis, skin graft reaction, acute pancreatitis, liver necroses (such as viral hepatitis), hemorrhagic, traumatic and septic shock, inflammatory states such as osteo- or rheumatoid arthritis, adjuvant arthritis, arthrosis, nephrotic (immunological) syndrome, systemic lupus erythematosis, adriamycin-induced heart toxicity, and neuroprotective brain tumors.

The preparations according to the invention are also suitable for prophylaxis and therapy of such diseases, caused by radical-mediated cell damage, as allergic reactions, atherosclerosis, inflammation under dermatological, inflammatory and psoriatic conditions, stress-induced ulcer, migraine, malignant hyperthermia, hypoxia syndrome, ischemic bowel syndrome, and the reduction of the necessary dose in the therapeutic application of radical-degrading enzymes, such as superoxide dismutase and catalase.

The medications according to the invention are also usable as antitumor active ingredients and are suitable for the prophylactic and therapeutic treatment of cardiac and circulatory disease states.

The invention will be described in further detail by means of the ensuing exemplary embodiments; the associated structural formula are shown below.

The number given in parentheses and underlined after the name of a respective compound refers to the associated structural formula below.

EXAMPLE 1

17α-4'-Hydroxyphenylmercaptomethyl-17-hydroxy-5α-androstan-3-one (1)

a) 17α-4'-Hydroxyphenylmercaptomethyl-3,3-dihydroxy-5α-androstan-17-ol 5 mmol (175 g) of 3,3-Dihydroxy-5α-androstan-17(S)-spirooxirane are dissolved at 30 to 40° C. while stirring in 10 ml of dry DMSO and then cooled back down to room temperature. In an argon atmosphere, 6.9 mmol (0.87 g) of 4-mercaptophenol and subsequently 6.9 mmol (0.77 g) of potassium tert.-butanylate are added. After a reaction time of approximately 5 hours at room temperature, the reaction mixture is stirred into ice-cooled dilute ammonium chloride solution, the white flakelike precipitate is removed by aspiration and dried in the dessicator over calcium chloride (in a vacuum), and the raw product is recrystallized from diisopropyl ether/methanol.

Yield: 0.91 g (38.4% of theoretical); melting point: 138 to 140° C.; $[\alpha]_D^{20}+13°$ (CHCl$_3$)

b) 17α-4'-Hydroxyphenylmercaptomethyl-17-hydroxy-5α-androstan-3-one 1.85 mmol (0.88 g) of 17α-4'-Hydroxyphenylmercaptomethyl-3,3-dimethoxy-5α-androstan-17-ol are suspended at room temperature in 10 ml of acetone, and 2 ml of 2n HCl are added. This produces a colorless solution. After approximately one hour, the reaction solution is stirred into ice-cooled dilute sodium hydrogen carbonate solution; the white precipitate is removed by suction, dried in the dessicator over phosphorus pentoxide (in a vacuum), and the raw product recrystallized from diisopropyl ether/methanol.

Yield: 0.22 g (27.8% of theoretical); melting point: 172 to 174° C.; $[\alpha]_D^{20}+32°$ (CHCl$_3$)

EXAMPLE 2

17α-Pentamethylselenomethyl-3-methoxy-1,3,5(10)-estratriene-17-ol (2)

3.35 mmol (1.0 g) of 3-methoxy-1,3,5(10)-estratriene-17 (S)-spirooxirane are dissolved at room temperature while stirring in 5 ml of dried THF and dripped in an argon atmosphere into Grignard solution, cooled to approximately 15° C. and freshly prepared from 12 mmol (0.30 g) magnesium, 10 mmol (2.27) of bromopentamethylbenzene, and 22 ml of THF. Immediately thereafter, 9 mmol (0.70 g) of selenium powder are added while stirring. The reaction mixture heats up slightly and gradually turns coffee-brown in color. The reaction mixture is held for approximately 2 hours at room temperature, then stirred into ice-cooled ammonium chloride solution; the precipitate is extracted with methyl-tert.-butyl ether; the extract is dried over sodium sulfate and inspissated in a vacuum.

The oily product is purified by column chromatography over silica gel 60 (0.040–0.063 mm) under pressure (elution with toluene/n-hexane 9:1) and ensuing recrystallization from acetone/methanol with the addition of diisopropyl ether.

Yield: 0.97 g (55.2% of theoretical); melting point: 144 to 146° C.; $[\alpha]_D^{20}+37.5°$ (CHCl$_3$)

EXAMPLE 3

17α-2',6'-Dimethyl-4'-hydroxyphenylmethyl-3-methoxyestra-1,3,5(10)-triene-17-ol (3)

3.35 mmol (1.0 g) of 3-methoxy-1,3,5(10)-estratriene-17 (S)-spirooxirane are dissolved at room temperature while stirring in 5 ml of dried THF and dripped in an argon atmosphere into Grignard solution, heated to approximately 40° C. and freshly prepared from 12 mmol (0.30 g) magnesium, 8.8 mmol (2.45 g) of 4-bromo-2,6-dimethyltrimethylsilyloxybenzene, and 10 ml of THF. The reaction mixture is stirred for approximately 4 hours at 60–65° C., then returned to room temperature, and the reaction mixture is stirred into ice-cooled ammonium chloride solution. The milklike sticky precipitate is extracted with methyl-tert.-butyl ether; the extract is dried over sodium sulfate and is inspissated in a vacuum. 2.4 g of oily raw product remain.

This product is dissolved in 20 ml of acetone, and 1 ml of 2n HCl is added. After approximately 2 h, the reaction mixture is stirred into ice-cooled NaHCO$_3$ solution; the yellow sticky precipitate is extracted with methyl-tert.-butyl ether; the extract is dried over sodium sulfate and inspissated in a vacuum, and the raw product obtained is purified by column chromatography over silica gel 60 (0.040–0.063 mm) under pressure (elution with toluene/acetic acid ethyl ether 9:1) and ensuing recrystallization from methanol with the addition of diisopropyl ether.

Yield: 0.15 g (10.7% of theoretical); melting point: 174 to 178° C.; $[\alpha]_D^{20}+44°$ (CHCl$_3$)

EXAMPLE 4

17α-4'-N,N-Dimethylaminophenylselenomethyl-3-methoxy-1,3,5(10)-estratriene-17-ol (4)

3.35 mmol (1.0 g) of 3-methoxy-1,3,5(10)-estratriene-17 (S)-spirooxirane are dissolved at room temperature while stirring in 5 ml of dried THF and dripped in an argon atmosphere into Grignard solution, cooled to 13 to 15° C. and freshly prepared from 12 mmol (0.30 g) magnesium, 9 mmol (1.8) of 4-bromodimethylaniline, and 15 ml of THF. Immediately after the addition of the oxirane has been completed, 9 mmol (0.70 g) of selenium powder are added while stirring, whereupon the reaction mixture heats up slightly and turns coffee-brown in color. The reaction mixture is held for approximately 4 hours longer at room temperature, then stirred into ice-cooled ammonium chloride solution; the precipitate is extracted with methyl-tert.-butyl ether; the extract is dried over sodium sulfate and inspissated in a vacuum.

The oily raw product is purified by column chromatography over silica gel 60 (0.040–0.063 mm) under pressure (elution with toluene) and ensuing recrystallization from methanol with the addition of diisopropyl ether.

Yield: 0.15 g (9% of theoretical); melting point: 110 to 111° C.; $[\alpha]_D^{20}$+39° (CHCl$_3$)

EXAMPLE 5

17α-4'-Hydroxyphenylmethyl-1,3,5(10)-estratriene-3,17-ol (5)

4.22 mmol (1.2 g) of 3-hydroxy-1,3,5(10)-estratriene-17(S)-spirooxirane are dissolved at room temperature while stirring in 10 ml of dry THF, and in an argon atmosphere are dripped into a freshly prepared Grignard solution of 28 mmol (0.68 g) of Mg, 24 mmol (5.88 g) of 4-bromotrimethylsilyloxybenzene and 18 ml of THF. After approximately 2 hours' reaction at room temperature, the reaction mixture is stirred for a further 3 hours at 50 to 60° C., later returned to room temperature and the reaction solution is stirred into acetonic hydrochloric acid and mixed after approximately 15 min with ice water; the extract is dried over sodium sulfate and inspissated in a vacuum.

The raw product is purified by column chromatography over silica gel Merck 60 (0.040–0.063 mm) under pressure (elution with toluene/acetic acid ethyl ester 9:1 to 7:3) and ensuing recrystallization from methanol.

Yield: 0.10 g (6.3% of theoretical); melting point: 238 to 242° C.;

EXAMPLE 6

17α-4'-Hydroxyphenoxymethyl-17-hydroxy-4-estrene-3-one (6)

3.0 mmol (1.0 g) of 3,3-dimethoxy-5(10)-estrene-17(S)-spirooxirane and 10 mmol (1.1 g) of hydroquinone are dissolved at 40 to 50° C. while stirring in 10 ml of dry DMSO, and in an argon atmosphere 10 mmol (1.12 g) of potassium tert.-butanylate are added in batches. The reaction mixture is held for approximately 7 hours at 50 to 60 ° C., subsequently returned to room temperature, and then stirred into ice-cooled ammonium chloride solution; the dark, sticky precipitate is extracted with methyl-tert.-butyl ether, and the extract is dried over sodium sulfate and inspissated in a vacuum.

0.9 g of raw product are dissolved in 10 ml of acetone, and 1 ml of 2n HCl is added. After approximately one hour, the reaction solution is stirred into ice-cooled sodium hydrogen carbonate solution; the white flakelike precipitate is removed by suction, dried in the dessicator over phosphorus pentoxide (in a vacuum), and the remaining raw product is purified by column chromatography over silica gel Merck 60 (0.040–0.063 mm) under pressure (elution with toluene/acetic acid ethyl ester 9:1) and ensuing recrystallization from diisopropyl ether/methanol.

Yield: 0.15 g (12.6% of theoretical); melting point: 195 to 197° C.;

EXAMPLE 7

17α-4'-N,N-Dimethylaminophenylmethyl-1,3,5(10),9(11)-estratetraene-3,17-diol (7)

9.0 mmol (2.54 g) of 3-hydroxy-1,3,5(10),9(11)-estratetraene-17(S)-spirooxirane are dissolved at room temperature while stirring in 15 ml of dry THF and dripped in an argon atmosphere into approximately 60 ml of a Grignard solution freshly prepared from 10 mmol (1.46 g) of Mg, 55 mmol (11.0 g) of 4-bromo-N,N-dimethylaniline and 60 ml of THF. After reaction for approximately 4 hours at room temperature, the reaction mixture is stirred into ice-cooled dilute ammonium chloride solution. The sticky precipitate is extracted with methyl-tert.-butyl ether, and the extract is dried over sodium sulfate. After inspissation in a vacuum, 9.0 g of a dark-green viscous oil remains, which is purified by column chromatography over silica gel Merck 60 (0.040–0.063 mm) under pressure (elution with toluene/acetic acid ethyl ester 9:1) and ensuing recrystallization from methanol.

Yield: 1.25 g (34.4% of theoretical); melting point: 130 to 132° C.; $[\alpha]_D^{20}$+74° (CHCl$_3$)

EXAMPLE 8

17α-4'-Hydroxyphenylmercaptomethyl-3,3-dimethoxy-5(10)-estrene-17-ol -3,3-dimethoxy-5(10)-estrene-17(S)-spirooxirane (8)

150 mmol (5.0 g) of 3,3-dimethoxy-5(10)-estrene-17(S)-spirooxirane are dissolved while stirring in 40 ml of dry DMSO, and in an argon atmosphere at room temperature 18.7 mmol (2.36 g) of 4-mercaptophenol and subsequently 18.7 mmol (2.1 g) of potassium-tert.-butanylate are added. After reaction for approximately 3 hours at room temperature, the mixture is stirred into ice-cooled dilute ammonium chloride solution; the white flakey precipitate is removed by suction and dried in the dessicator over sodium hydroxide (in a vacuum), and the raw product is recrystallized from diisopropyl ether/methanol.

Yield: 3.9 g (56.8% of theoretical); melting point: 155 to 157° C.; $[\alpha]_D^{20}$+105° (CHCl$_3$)

EXAMPLE 9

3,17β-Dihydroxy-17α-4'-N,N-dimethylaminophenyl-1,3,5(10)-estratriene (9)

A suspension of 4.8 mmol (1.2 g) of dried Ce(III) chloride in 5 ml of THF is added drop by drop, while stirring intensively, in an argon atmosphere at −10° C. to 7.8 mmol (7.8 ml) of a Grignard compound freshly prepared from 14.6 mmol (350 mg) of magnesium, 12 mmol (2.4 g) of p-bromo-N,N-dimethylaniline and 12 ml of dry THF. After approximately 45 minutes, 1.4 mmol (380 mg) of estron is added and stirred for 1 hour at −5 to 0° C. and then left to warm up to room temperature. The mixture is stirred into 50 ml of saturated ammonium chloride solution. The phases are separated, and the aqueous phase is re-extracted with methyl-tert.-butyl ether. The combined organic phases are washed with water, dried over sodium sulfate, and evaporated in a vacuum.

The residue is purified by flash chromatography over 40 g of silica gel (0.040 to 0.063 mm; eluent n-hexane/acetic acid ethyl ester 2:1 v/v) and recrystallized from acetone. One obtains 354 mg of a nearly white crystalline substance.

Melting point: 212 to 220° C.

EXAMPLE 10

3-Hydroxy-17-4'-N,N-dimethylaminophenyl-1,3,5(10),16-estratetraene (10)

0.64 mmol (250 mg) of 3β,17β-Dihydroxy-17-4'-N,)N-dimethylaminophenyl-1,3,5(10)-estratriene are dissolved in 25 ml of acetone at 50° C. and, after the addition of 1.8 ml of 2N hydrochloric acid, stirred for 8 hours. Next, at room temperature, 20 ml of saturated sodium hydrogen carbonate solution are added. After 30 minutes, the acetone is evaporated off in a vacuum, and the aqueous residue is extracted with 60 ml of methyl-tert.-butyl ether. The organic phase is washed with water, dried over sodium sulfate, filtered, and evaporated in a vacuum. The residue is crystallized out of acetone/n-hexane.

Yield: 142 mg of crystalline substance; melting point 188 to 193° C.; needles.

EXAMPLE 11

3,17β-Dihydroxy-6,4'-N,N-dimethylaminophenyl-1,3,5(10),6-estratetraene (11)

In an argon atmosphere and while stirring, 3.8 mmol (3.8 ml) of a Grignard solution, freshly prepared from 14.6 mmol (350 mg) of magnesium, 12 mmol (2.4 g) of p-bromo-N,N-dimethylaniline and 12 ml of dry THF, are added at −10° C. to 3 mmol (0.74 g) of dried cerium(III) chloride suspended in 5 ml of dry THF. After 15 minutes, 0.8 mmol (350 mg) of 3,17-bis-trimethylsilyloxy-6-oxo-1,3,5(10)-estratriene, dissolved in 5.6 ml of dry THF, is added. stirring is done for 1 hour at −5° C. After heating to room temperature, the mixture is stirred into 50 ml of saturated ammonium chloride solution. After phase separation, washing is done with saturated ammonium chloride solution and water. The aqueous phases are re-extracted with methyl-tert.-butyl ether. The combined organic phases are mixed with 0.5 ml of 6N hydrochloric acid and stirred for 1 hour at room temperature. 50 ml of water are then added and the phases are separated. Once the pH value of the aqueous phase is adjusted to 8, this phase is extracted with methyl-tert.-butyl ether. The combined organic phases are dried over sodium sulfate, filtered, and inspissated in a vacuum.

The raw product is purified by column chromatography over 16 g of silica gel (0.040 to 0.063 mm; eluent n-hexane/acetic acid ethyl ester 70:30 v/v) and finally crystallized from acetone. One obtains 113 mg of a nearly white crystalline substance.

Melting point: 215 to 220° C.

EXAMPLE 12

3,17β-Dihydroxy-6,3',5'-dimethyl-4-hydroxyphenyl-1,3,5(10),6-estratetraene (12)

Under conditions of moisture exclusion and in an argon atmosphere, 6 mmol (6 ml) of a Grignard solution, freshly prepared from 12.1 mmol (295 mg) of magnesium, 10 mmol (2.7 g) of 1-bromo- 3,5-dimethyl-4-trimethylsilyloxybenzene and 13 ml of THF, are added drop by drop at −10°C. to 6 mmol (1.5 g) of dried cerium(III) chloride suspended in 7 ml of dry THF. Next, 1.4 mmol (600 mg) of 3,17β-bis-trimethylsilyloxy-6-oxo-1,3,5(10)-estratriene is added and stirred for a further 2 hours at −10° C.

The reaction mixture is then diluted with 45 ml of methylene chloride, mixed with 20 ml of 6N HCl, and stirred for one hour at room temperature.

After phase separation and reextraction of the aqueous phase with methylene chloride, the mixture is washed with saturated sodium hydrogen carbonate solution and water, dried over sodium, sulfate, and evaporated in a vacuum. The raw product, obtained as a brown oil, is purified by column chromatography over silica gel (0.040 to 0.063 mm; n-hexane/acetic acid ethyl ester 70:30 v/v) and crystallized from methylene chloride.

Yield: 312 mg of yellow crystalline substance. Melting point: 172 to 176° C.

EXAMPLE 13

17β-Hydroxy-6β-4'-hydroxyphenyl-3-oxo-4-androstene (13)

1.25 mmol (500 mg) of 5α,17β-Dihydroxy-6β-4'-hydroxyphenyl-3-oxo-4-androstane (14) are dissolved at room temperature in an argon atmosphere in 25 ml of 1% methanolic potassium hydroxide solution, heated to 45° C., and stirred for 3 hours.

After cooling down to room temperature, the reaction solution is neutralized with 10% aqueous acetic acid, and the product, 17β-Hydroxy-6β-4'-hydroxyphenyl-3-oxo-4-androstene is precipitated with ice water. After removal by suction, 361 mg of 17β-Hydroxy-6β-4'-hydroxyphenyl-3-oxo-4-androstene is obtained in the form of a light-colored crystalline sediment. The raw product is crystallized from acetone. 130 g of nearly white crystals are obtained. Melting point: 230 to 238° C.

EXAMPLE 14

5α,17β-Dihydroxy-6β-4'-hydroxyphenyl-3-oxo-4-androstane (14)

a) 6β-4'-tert.-butyldimethylsilyloxyphenyl-5α,17β-dihydroxy-3,3-ethylenedioxyandrostane Under conditions of moisture exclusion and in an argon atmosphere, 2.4 mmol (850 mg) of 5,6α-epoxy-3,3-ethylenedioxy-17β-hydroxyandrostane are added while stirring at −10°C. to a Grignard solution, prepared from 25.4 mmol (618 mg of magnesium, 21.2 mmol (6.1 g) of p-bromo-tert.-butyldimethyloxysilylbenzene and 56 ml of dry tetrahydrofuran, previously mixed with 0.64 mmol (130 mg) of copper bromide dimethylsulfide. This is left to react for approximately 2 hours at 0 to 5° C. and then is stirred into 60 ml of saturated ammonium chloride solution.

After phase separation and inspissation in a vacuum, the aqueous-oily residue is adsorbed in methylene chloride, washed with saturated ammonium chloride solution and the water, dried over magnesium sulfate, and re-inspissated in a vacuum.

The raw product is purified by column chromatography over silica gel (0.040 to 0.063 mm; acetic acid ethyl ester/n-hexane 30:70 v/v).

1.28 g of a white foam are obtained (NMR (CDl$_3$, 300 MHz; ppm): 0.19 (s,6H,Si—CH$_3$); 0.67 (s,3H,18-H); 0.86 (s,3H,19-H); 0.98 (s,9H,t-C$_4$H$_9$); 2.89 (m,1H,6α-H); 3.70 (m,1H,17α-H); 4.02 (m,4H,OCH$_2$CH$_2$O); 6.72 (d,J=8 Hz,2'- and 6'-H); 7.26 (d,J=8 Hz,3'- and 5'-H).

b) 5α,17β-Dihydroxy-6β-4'-hydroxyphenyl-3-oxo-4-androstane (14)

2.3 mmol (1.28 g) of 6β-4'-tert.-butyldimethylsilyl-oxyphenyl-3,3-ethylenedioxy-5α,17β-dihydroxyandrostane are dissolved while stirring at room temperature in 128 ml of dry THF and mixed with 11.6 mmol (3.65 g) of tetrabutyl ammonium fluoride. After one hour of continuous stirring, 2.6 ml of 6N hydrochloric acid are added. The mixture is left to stand overnight at room temperature and is then inspissated in a vacuum. The residue is adsorbed in acetic acid ethyl ester and washed with saturated sodium hydrogen carbonate solution and water.

After drying over magnesium sulfate and filtering, evaporation in a vacuum is done; the residue is crystallized from methylene chloride; and 830 mg of crystalline 5α,17β-Dihydroxy-6α-4'-hydroxyphenyl-3-oxo-4-androstane. Melting point: 155 to 162° C.

Investigations of the Pharmacological Efficacy of the Radical-Scavenger Substances Testing of the substances for inhibitory effect with regard to lipid peroxidation was carried out as follows:

Reaction Mixture 1 ml of biological specimen (containing 0.1 mg of plasma membranes), including Fenton's reagent and drug.

The total volume of 1 ml is divided into 0.01 to 0.02 ml synaptosomal membrane fraction; 0.1 ml iron(II) chloride (2 mM); 0.1 ml hydrogen peroxide (2 mM), replenish to 1 ml with 0.9% NaCl (not PBS) and ethanol or DMSO as a vehicle for the drug to be tested.

Procedure

The reaction mixture is incubated for 30 min at 37° C., then stopped with 2 ml of reagent A and incubated for 10 min at a constant 80° C. After cooling down in an ice bath (10 min), the specimen is centrifuged in a cooling centrifuge (1000×g; 40° C.). The residue (stable for up to 2 h) is measured at 535 nm against the blind value, which except for the membrane fraction contains all the reagents.

As a comparison value, the mixture is used that contains, besides the membrane fraction, NaCl and in a given case vehicle with the same proportions.

Composition of Reagent A

15% (w/v) trichloroacetic acid (15 g); 0.375% (w/v) thiobarbituric acid (375 mg); 0.25 n HCl (2.11 ml of concentrated HCl)

in 100 ml of aqueous solution.

Test Substances

The test substances are preferably mixed in ethanol as 20 millimolar parent solutions and diluted accordingly. The dosage range from 1 to 150 μmol was tested.

A suitable standard substance is included in all the test kits.

Evaluation Parameters

Dosage-action analysis of the test substances.

Ascertainment of the lipid peroxidation inhibition values with at least five substance concentrations in the inhibition range from 30 to 70%, referred to the test values without substance effect.

Testing of the substances for inhibitory action with regard to LDL oxidation, by the method of Esterbauer et al (1988), was carried out as follows:

Reaction Mixture 2 ml of biological specimen (containing 0.5 mg LDL, isolated from human whole blood, including 10 μmol $CuSO_4$ and from 1 to 150 μmol of test substance and ethanol as a vehicle for the drug to be tested) in the cell-free medium PBS.

Procedure

The reaction mixture is incubated at room temperature over a period of at least 8 h and followed spectral photometrically (the absorption maximum of the oxidized LDL is at 234 nm). In accordance with the extinction changes, recorded at the measurement wavelength of 234 nm, in the presence or absence of test substances or in comparison of the native and the oxidized LDL, definitive statements on the influence on the oxidized LDL by the action of the test substance.

Test Substances

The test substances are preferably mixed in ethanol as 20 millimolar parent solutions and diluted accordingly. The dosage range from 1 to 150 μmol was tested.

A suitable standard substance is included in all the test kits.

Evaluation Parameters

Dosage-action analysis of the test substances.

Ascertainment of the LDL oxidation inhibition values, demonstrated as a delay in LDL oxidation in the form of a chronologically prolonged lag period (in min).

We claim:

1. A compound selected from the group consisting of [6β-4'-Hydroxyphenyl-5α,17β-dihydroxyandrostan-3-one,]
17α-4'-N,N-Dimethylaminophenylestra-1,3,5(10)-triene-3,17-diol,
17α-4'-N,N-Dimethylaminophenylmethylestra-1,3,5(10)-triene-3,17-diol,
17α-4'-N,N-Dimethylaminophenylmethyl-3-methoxyestra-1,3,5(10)-triene-17-ol,
17α-4'-Hydroxyphenylmethylestra-1,3,5(10)-triene-3,17-diol,
17α-4'-Hydroxyphenylmercaptomethylestra-1,3,5(10)-triene-3,17-diol,
17α-4'-Hydroxyphenylmercaptomethyl-3-methoxyestra-1,3,5(10)-triene-17-ol,
17α-4'-Hydroxyphenylmethyl-3-methoxyestra-1,3,5(10)-triene-17-ol,
17α-2',6'-Dimethyl-4'-hydroxyphenylselenomethyl-3-methoxyestra-1,3,5(10)-triene-17-ol,
17α-4'-N,N-Dimethylaminophenylselenomethyl-3-methoxyestra-1,3,5(10)-triene-17-ol,
17α-2',6'-Dimethyl-4'-hydroxyphenylmethyl-3-methoxyestra-1,3,5(10)-triene-17-ol,
17α-2',6'-di-tert.-butyl-4'-hydroxyphenylmethyl-3-methoxy-estra-1,3,5(10)-triene-17-ol and
17α-2',6'-di-tert.-butyl-4'-hydroxyphenylselenomethyl-3-methoxyestra-1,3,5(10)-triene-17-ol [and 6α-4'-Hydroxyphenylmercaptomethyl-17-hydroxyandrost-4-ene-3-one].

2. A pharmaceutical composition containing an effective amount of a steroid compound having a radical-attracting aromatic substituent for prophylaxis and therapy of radical-mediated cell damage and/or diseases caused by radical-mediate cell damage together with a pharmaceutically acceptable vehicle or diluent or pharmaceutical adjuvant;

wherein said steroid compound having a radical-attracting aromatic substituent is selected from the group consisting of
17α-4'-N,N-Dimethylaminophenylmethylestra-1,3,5(10)-triene-3,17-diol,
17α-4'-N,N-Dimethylaminophenylestra-1,3,5(10)-triene-3,17-diol,
17α-4'-N,N-Dimethylaminophenylmethyl-3-methoxyestra-1,3.5(10)-triene-17-ol,
17α-4'-Hydroxyphenylmethylestra-1,3,5(10)-triene-3,17-diol,
17α-4'-Hydroxyphenylmercaptomethylestra-1,3,5(10)-triene-3,17-diol,
17α-4'-Hydroxyphenylmercaptomethyl-3-methoxyestra-1,3,5(10)-triene-17-ol,
17α-4'-Hydroxyphenylmethyl-3-methoxyestra-1,3,5(10)-triene-17-ol,
17α-2',6'-Dimethyl-4'-hydroxyphenylselenomethyl-3-methoxyestra-1,3,5(10)-triene-17-ol,
17α-4'-N,N-Dimethylaminophenylselenomethyl-3-methoxyestra-1,3,5(10)-triene-17-ol,
17α-2',6'-Dimethyl-4'-hydroxyphenylmethyl-3-methoxyestra-1,3,5(10)-triene-17-ol,
17α-2',6'-di-tert.-butyl-4'-hydroxyphenylmethyl-3-methoxyestra-1,3,5(10)-triene-17-ol and 17α-2',6'-di-tert.-butyl-4'-hydroxyphenylselenomethyl-3-methoxyestra-1,3,5(10)-triene-17-ol.

3. 17α-4'-hydroxyphenylmercaptomethylestra-1,3,5(10)-triene-3,17-diol.

4. A pharmaceutical composition containing an effective amount of 17α-4'-hydroxyphenylmercaptomethylestra-1,3,5(10)-triene-3,17-diol for prophylaxis and therapy of radical-mediated cell damage and/or diseases caused by radical-mediate cell damage together with a pharmaceutically acceptable vehicle or diluent and/or pharmaceutical adjuvant.

* * * * *